United States Patent [19]
Trawoger et al.

[11] Patent Number: 5,484,282
[45] Date of Patent: Jan. 16, 1996

[54] CENTRIFUGE SEPARATOR FOR SEPARATING A MIXTURE OF WASTE SOLID AND WASTE LIQUID

[76] Inventors: Werner Trawoger, Huebe 26; Bruno Pregenzer, Huebe 30, both of A-6173 Oberperfuss, Austria

[21] Appl. No.: 129,203
[22] PCT Filed: Apr. 1, 1992
[86] PCT No.: PCT/AT92/00043
    § 371 Date: Oct. 8, 1993
    § 102(e) Date: Oct. 8, 1993
[87] PCT Pub. No.: WO92/18062
    PCT Pub. Date: Oct. 29, 1992

[30] Foreign Application Priority Data

Apr. 12, 1991 [AT] Austria .................................. 775/91

[51] Int. Cl.⁶ .................................. A61C 17/06
[52] U.S. Cl. .................................. 433/92; 494/35; 494/42
[58] Field of Search .................................. 494/31, 32, 34, 494/35, 36, 42, 43, 44, 63; 210/380.1; 433/92

[56] References Cited

U.S. PATENT DOCUMENTS

| | | | |
|---|---|---|---|
| 4,564,374 | 1/1986 | Hofmann | 433/92 X |
| 4,753,632 | 6/1988 | Hofmann et al. | 494/43 |
| 5,018,971 | 5/1991 | Trawoger et al. | 433/92 |

FOREIGN PATENT DOCUMENTS

| | | |
|---|---|---|
| 0224232 | 11/1986 | European Pat. Off. . |
| 0300439 | 7/1988 | European Pat. Off. . |
| 0400431 | 5/1990 | European Pat. Off. . |
| 3231272 | 2/1984 | Germany .................................. 433/92 |
| 8702001 | 2/1987 | Germany . |
| 3601254 | 7/1987 | Germany .................................. 433/92 |
| 427988 | 5/1983 | Sweden . |
| WO8603669 | 7/1986 | WIPO . |
| WO8904152 | 5/1989 | WIPO . |

*Primary Examiner*—David Scherbel
*Assistant Examiner*—Charles E. Cooley
*Attorney, Agent, or Firm*—Lorusso & Loud

[57] ABSTRACT

A separator including a full-casing centrifuge and detachably mounted settler tank for solids which run off under action of gravity after centrifuge phase. An inlet for mixture to be separated is located in top of settler tank. A pump with suction tube which extends into settler tank is connected by a line to centrifuge inlet port and conveys all liquid arising, from which at least great particles have already settled out into centrifuge.

11 Claims, 5 Drawing Sheets

5,484,282

CENTRIFUGE SEPARATOR FOR SEPARATING A MIXTURE OF WASTE SOLID AND WASTE LIQUID

BACKGROUND OF THE INVENTION

1. Field of the Invention

The present invention relates to a separator for separating a mixture of solid and liquid, in particular waste water originating from dental practice, with an inlet for the mixture that is to be separated, with an outlet for the liquid that has been separated off, with a full-casing centrifuge which has an inlet opening arranged on the top, a transfer opening that is associated with the outlet for the liquid, and a drain for the solids, with a removable settling tank that is arranged beneath the outlet for the solids and used for the solids that run off after each centrifuging phase as a result of gravity, with a residual fluid fraction, with a pump that has a suction pipe that extends downwards into the settling tank to a point above a maximum preset sedimentation level (into the settling tank), and with a line that connects the pressure side of the pump with the inlet opening of the centrifuge.

2. Description of the Related Art

A separator of this type is described, for example, in FIG. 3 of WO-A-89/04152. In this separator, the inlet for the mixture that is to be separated, which originates, for example, from a dental suction system or from a rinse basin, is located in the separator on the top of the centrifuge and opens out into a mixture inlet chamber from which it moves into the centrifuge. The solids that flow out together with the residual liquid collect in the settling tank, from which the remaining liquid is moved upwards and into the mixture inlet by means of the pump. When a preset level of sediment is reached, the settling tank is removed and emptied and replaced by an empty tank.

It has been shown that a primary screen is useful or even necessary in the feed line to the mixture inlet in order to prevent particles that are too large from entering the centrifuge. Such particles come mainly from the rinsing basin, when the mouth is rinsed. Larger particles of this kind, such as bone or tooth fragments, pieces of amalgam, or even cellular material, can unbalance the centrifuge if they are not removed, or can impair the degree of purity of the liquid.

For this reason, it is the task of the present invention to so configure a separator of the type described in the introduction hereto that only particles of solid material that are of a size that can be processed without any difficulty are allowed into the centrifuge.

SUMMARY OF THE INVENTION

According to the present invention, this has been achieved in that the inlet for the mixture that is to be separated is provided on the top of the settling tank.

In this way, the mixture first moves into the settling tank, within which mainly the larger particles sink to the bottom so that the pump removes only the remaining liquid and those small and very small particles of solid that could not be separated off because the dwell time is too short or which, because of a momentary and very large quantity of water, have once again been stirred up, and then passes it to the centrifuge.

Thus, the pump not only returns the residual liquid from the centrifuge to the centrifuge; it also returns all of the liquid that is recovered. The arrangement of a sedimentation tank ahead of the centrifuge is known from SE-B-427 988, although the sedimentation tank, which is only indicated therein, is provided with an overflow that opens out into the centrifuge and with an inlet that is close to the bottom, so that essentially this is only a primary screen. The solids are collected in a second tank that is located beneath the centrifuge.

In general, separators of this kind are built in apparatuses used in dental chairs or into other items of equipment used in a dental practice and which, for this reason require a mounting, when there must be sufficient free space to remove the settling tank from beneath the apparatus. One embodiment according to the present invention is such that the separator has an installation case with transit-type openings, on which the centrifuge housing is arranged and on which the settling tank is held so that it can be removed from below, the mixture inlet being arranged in the installation housing.

This embodiment not only makes it simpler to install the separator, especially when it is to be retrofitted to existing work places, because the installation casing can be configured to match the particular local conditions; in addition, it also makes it possible to select the dimensions of the settling tank, principally its length and width, regardless of the dimensions of the centrifuge housing to which the settling tank is joined when it is mounted directly onto the centrifuge.

In order to provide for a very compact embodiment it is preferred that the centrifuge housing tapers down towards the installation housing and the mixture inlet is provided in the area of the installation housing that results from the taper in the centrifuge housing. Then, an angle piece that can be pivoted about an axis that is perpendicular to the installation housing can be provided in this recessed area and used for a connector to the mixture feedline which can be turned in any direction. It is preferred that the pump be arranged coaxially beneath the centrifuge; this can have a dedicated drive motor. However, the pump and the centrifuge can also be powered by a motor that is arranged between them because the pump has to be running at the same time as the centrifuge.

In another preferred embodiment, the suction pipe for the pump is fitted with screening baffles in order to deflect the mixture coming in through the mixture inlet. These can be arranged on both sides, so as to be stepped away from the mixture inlet, the final baffle then extending vertically. This means that direct entry of the mixture to the suction pipe will be prevented even at very high flow rates of up to 12 liters/min. and more, which is to say when the proportion of liquid is extremely high. A centrifuge housing that tapers towards the installation housing also means that the connecting line to the inlet opening of the centrifuge can be accommodated in the open area of the assembly housing that is left by the taper.

The separator according to the present invention can be used both within the vacuum system of a dental suction system and also outside such a system. When it is used outside the vacuum system, the mixture inlet in the installation housing is preferably provided with a non-return valve that is associated with the pressure side of an auxiliary pump. The auxiliary pump serves to remove the mixture that is to be separated against the force of the vacuum generated by an air separator system that is incorporated ahead of it, so that the suction that is used for emptying the air separator system does not have to be interrupted.

When used within the vacuum system, a non-return valve is provided at the liquid outlet of the centrifuge or in the drain line that is connected to it. Here, too, an auxiliary pump is used to overcome the suction vacuum in the separator. This auxiliary pump can be incorporated, for example, in the drain line, although its effect can also be achieved in that the centrifuge is fitted with pump veins in the vicinity of the liquid transfer opening.

DESCRIPTION OF THE PREFERRED EMBODIMENTS

The present invention is described in greater detail below on the basis of the drawings appended hereto, without being restricted thereto.

Figure 1:
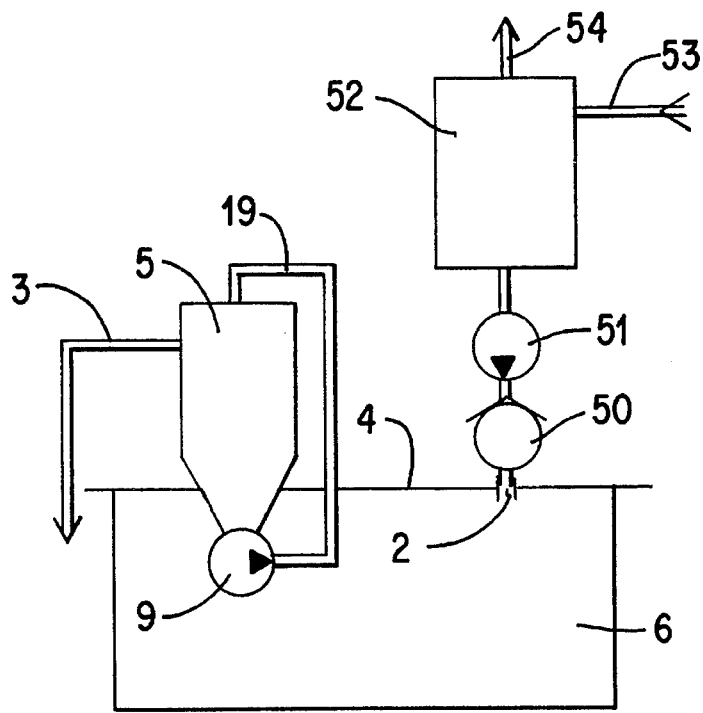
FIGS. 1 and 2 are diagrammatic drawings of two different separator systems that are used to separate suction air, solids and liquids.
Figure 2:
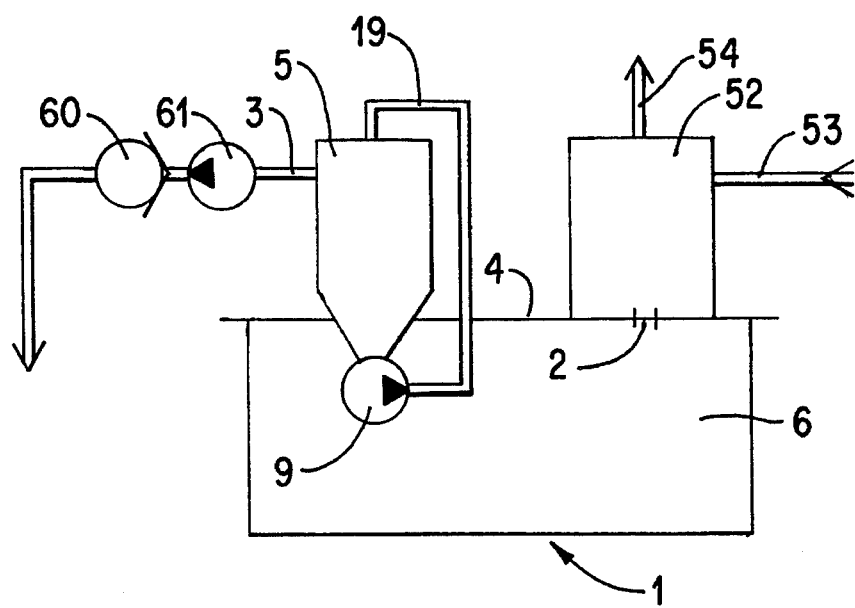

Separator systems as in FIGS. 1 and 2 consist of an air separator device 52 with a mixture feedline 53 and a clean-air line 54 that leads to a suction pump, and a separator 1 that is used to separate the liquid and the solids. In the embodiment that is shown in FIG. 1, the separator 1 according to the present invention is located outside the vacuum system, i.e., there is an auxiliary pump 51 and, on the back of this pump there is a non-return valve 50, between the air separator device 52 and the mixture inlet 2 of the separator 1. In the embodiment shown in FIG. 2, the separator 1 is within the vacuum system and the liquid outlet 3 has an auxiliary pump 61 and the pressure side non-return valve 60.

Figure 3:
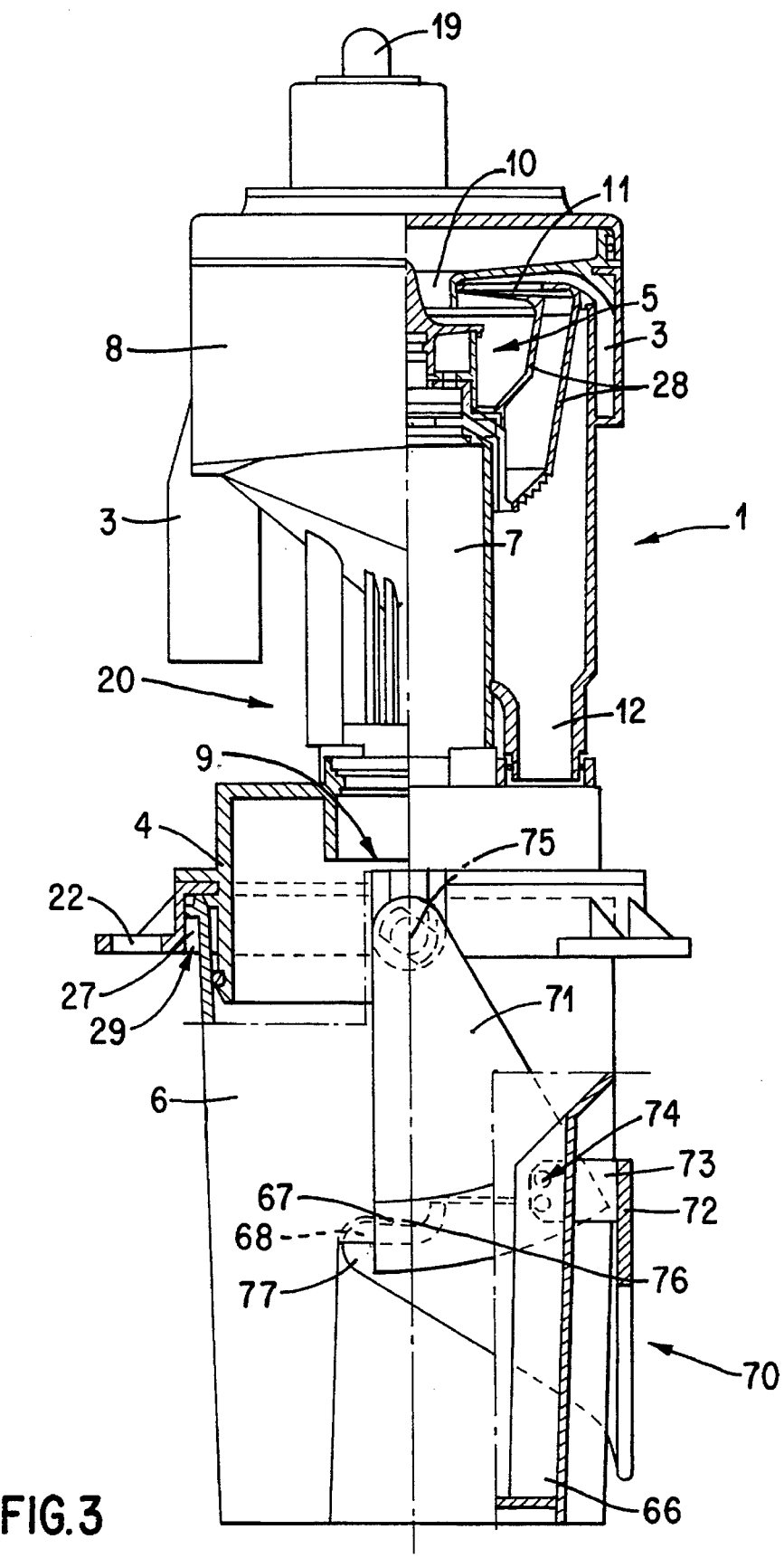
FIGS. 3 and 4 are vertical cross-sections through a separator according to the present invention.
Figure 4:
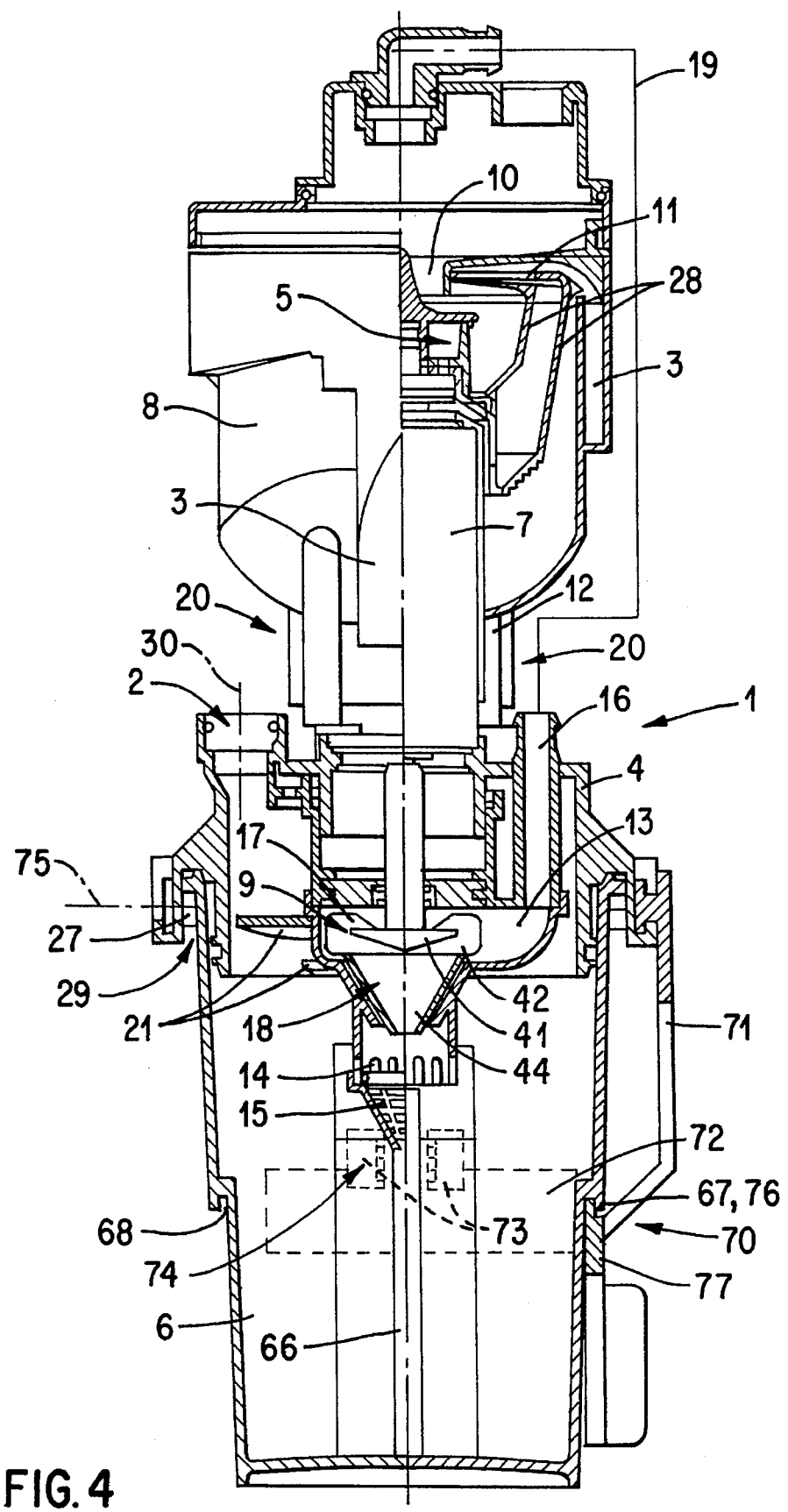
Figure 5:
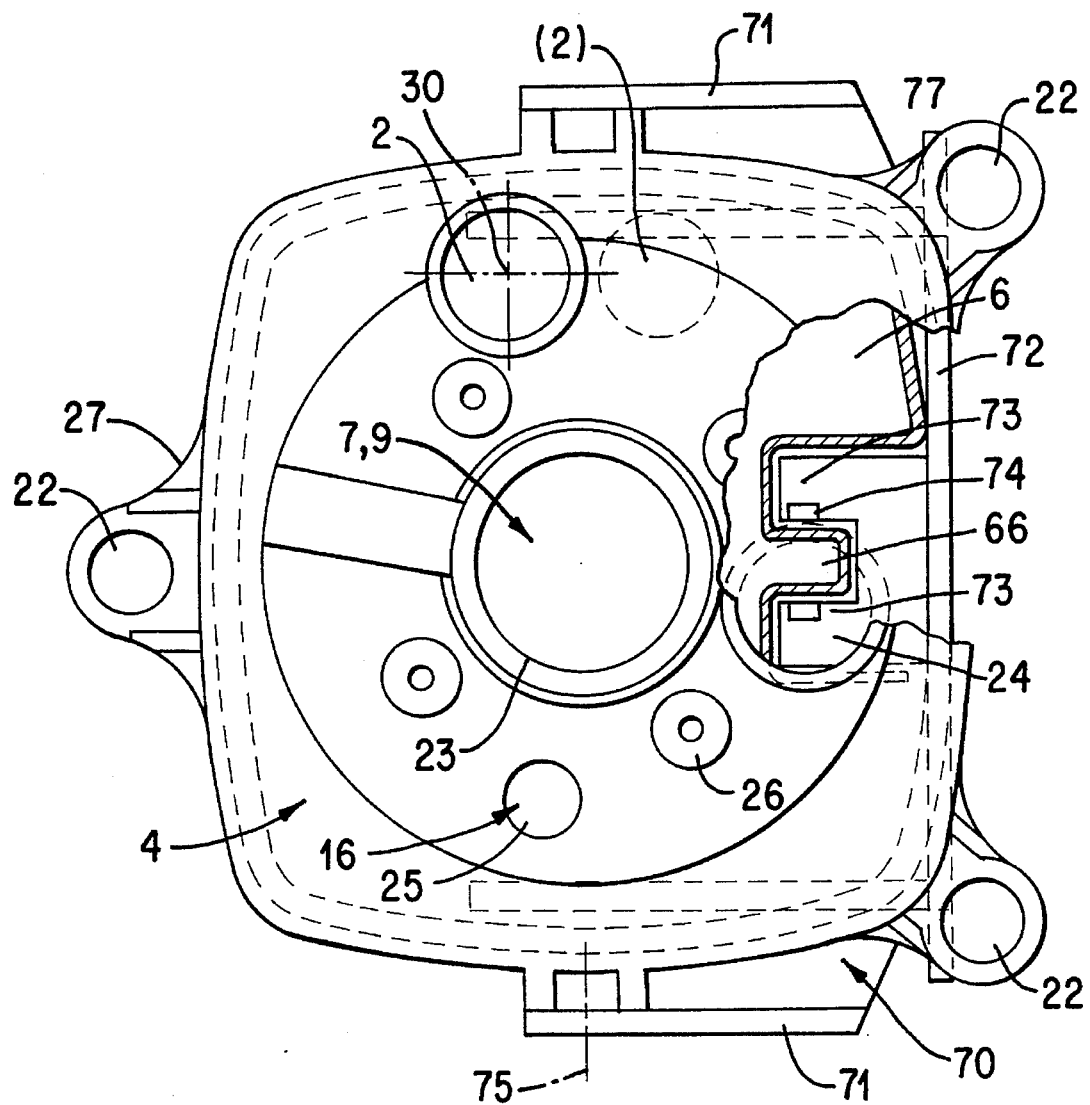
FIG. 5 is a plan view of an installation housing.
Figure 6:
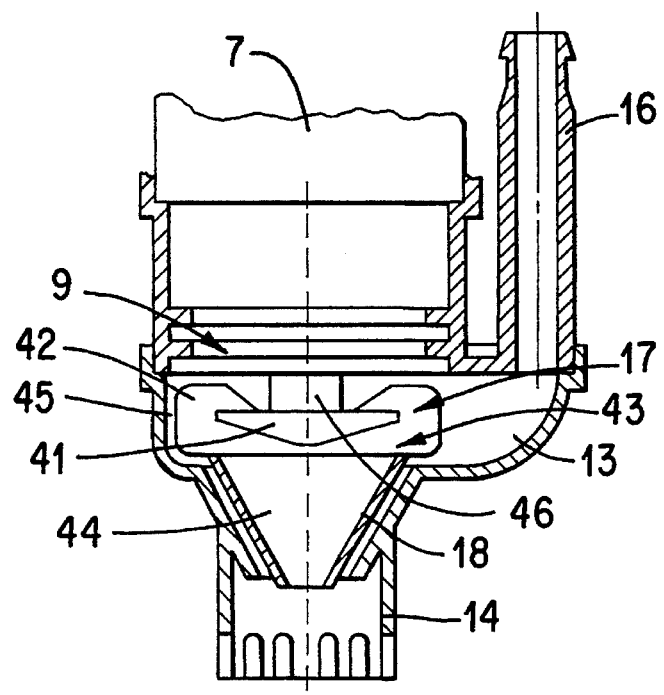
FIG. 6 is a larger scale drawing of the pump that is used in the separator.
Figure 7:
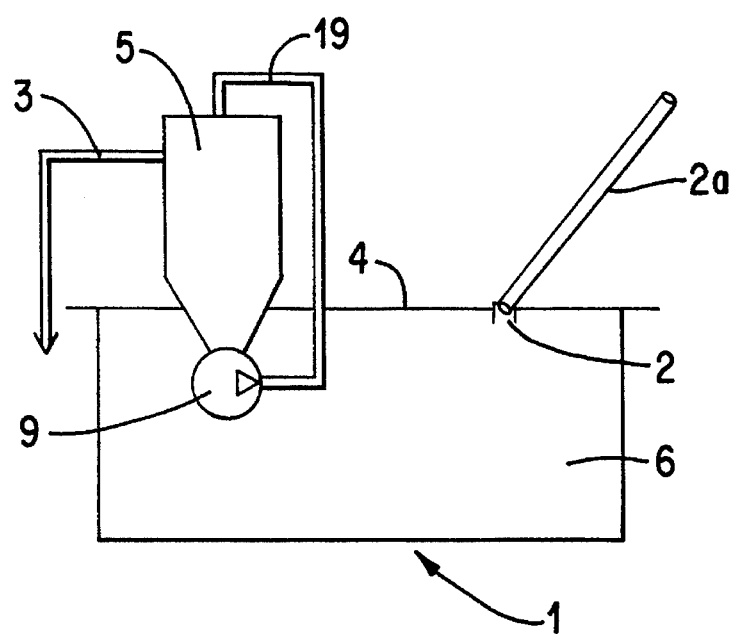
FIG. 7 is a diagrammatic drawing of the separator shown in FIG. 1 with an angular connector.

The separator 1 comprises a settling tank 6 that is used to sediment the solids, and a full-casing centrifuge 5 that is incorporated in the through-flow direction, on the settling tank 6. Both are arranged on an installation housing 4 that can be mounted on a dental chair or the like, so that the settling tank 6 is mounted so as to be removable from the installation housing 4 from below, as can be seen in greater detail in FIGS. 3 and 4. The installation housing 4 is provided with attachment drillings 22 that are provided, in particular, on a dedicated adaptor 27. Appropriate adaptors 27 are available for particular installations and the installation housing 4 can be provided with these. There are other transit-type openings in the installation housing 4: there is an opening 23 used to accomodate the motor 7 for the centrifuge 5 and for a pump 9, an opening 24 for insertion of the solids drain 12 of the centrifuge 5, an opening 25 for routing a connection line 19, which is only shown diagrammatically, between the pump line and the centrifuge 5, the drillings 26 for mounting bolts for the joint attachment of the centrifuge housing 8 and of the pump housing 13, and the mixture inlet 2 through which the mixture coming from the air separator device 52 and/or a rinsing basin can be introduced into the separator 1. As is shown, a second mixture inlet (2) can be provided so that each feedline can be attached to its own dedicated mixture inlet 2 (2). The centrifuge housing 8, which is fixed to the installation housing 4, is tapered in its lower part, the motor 7 being arranged centrally, and in addition it also contains the two centrifuge containers 28 of the full casing centrifuge 5, these being arranged one inside the other. An inlet 10 for the mixture that is pumped up through the connecting line 19 from the settling tank 6 opens out into the inner centrifuge container 28, and the outer centrifuge container 28 has a transfer opening 11 through which the clarified liquid moves into the liquid outlet 3. When the centrifuge 5 is stationary, solids flow downwards under gravity and pass through the eccentrically arranged solid drain 12, through the opening 24, into the settling tank 6. An angular connector (2) is inserted into the mixture inlet 2 (2) of the installation housing 4 so as to be rotatable. Both the mixture inlet 2 (2) and the opening 25 for the connector line 19 are located in the space 20 that results from the taper of the centrifuge housing 8, which is to say within the space required for the centrifuge 5, and this results in an extremely compact and space-saving embodiment.

A groove 29 in the installation housing 4 that is open underneath serves as a slide for the setting tank 6. This is fixed in place by means of a stirrup-shaped locking element 70 that is mounted so as to be able to pivot about a shaft 75 on the outside wall of the groove 29. The locking element 70 has two pivoting arms 71 that extend at the sides outside the settling tank 6 and a cross-piece 72 that joins these. A bar 77 that is parallel to these is associated with each pivot arm 71 and this fits in a pocket 68 in the settling tank 6 when in the closed position. A detent recess 76 that is provided in at least one bar 77 enters into detent on a cam 67 in the pocket 68 of the settling tank 6. The settling tank 6 is made from transparent plastic and has longitudinal rib 66 that projects on a wall that faces the cross-piece 72. The cross-plate 72 has projecting tabs 73 that are parallel to the side walls of the longitudinal rib 66, on which a sensing device 74 is formed. This includes at least one or, in the embodiment shown, two light barriers such that each beam of light passes through the longitudinal rib 66 and permits measurement of the level of the sedimented solids. The lower light barrier responds when the level to which the container is full reaches 95% of the maximum and emits a warning signal, whereas when the second upper light barrier that indicates the maximum filling level responds, the separator, preferably the whole of the suction system, is shut down. In order to replace the settling tank, the locking element 70 is swung upwards so that the bars 77 release the settling tank 6, which can then be removed downwards. The sensor system 74 could also comprise additional sensor elements to detect the two lines levels of liquid that collect above the solids at which the motor 7 would be switched on and off.

The pump housing 13 is secured to the underside of the installation housing 4 and has a projecting connector 16 that extends upwards through the opening 25 in the installation housing 4, so that the connecting line 19 can be installed once the pump 9 and the centrifuge 5 have been secured. A central suction pipe 14 extends downwards from the pump housing 13; in its upper part this tapers conically; in the middle it is cylindrical; and in the bottom part it has openings around its periphery. A protective screen 15 is fixed at least to the side of the mixture inlet 2 on the suction pipe 14. The pump 9 incorporates an impeller wheel 17 that comprises a hub 41 that is mounted on the drive shaft 46, vanes 42 that extend radially from this, and a hollow truncated cone 18 that extends downwards into the conical part of the suction pipe 14. The hollow truncated cone 18 is secured to the lower narrow side of the vanes 42 that project axially downward beyond the hub 41. The diameter of the hub 41, the lower surface of which is conical, is approximately the same as the maximum diameter of the truncated hollow cone 18. Slits 43 are formed between the vanes 42 through the mounting of the truncated hollow cone 18 on the vanes 42, between the hub 41 and the upper edge of the truncated hollow cone 18, and these force the liquid that is sucked out of the settling tank into the circulating chamber 45 that is formed in the pump housing 13.

We claim:

1. A separator for separating a dental waste mixture of solids and liquids, said separator comprising: a separator housing having a mixture inlet for the mixture of solids and liquids that are to be separated, an outlet for discharging separated liquids, and a settling tank collecting separated liquids up to a preset maximum settling level, said mixture inlet opening into a top region of the settling tank; a full casing centrifuge arranged in the separator housing and having a top inlet opening, a bottom drain opening vertically discharging by gravity solids and liquid residues into the settling tank after each centrifuging phase, and a top liquid outlet passing cleaned liquids into the discharge outlet of the separator housing, said settling tank being removably arranged on the separator housing below the bottom drain opening; a pump means having a suction pipe extending downwards into the settling tank; and a connecting line connecting the pump means with the top inlet opening of the centrifuge.

2. A separator as defined in claim 1, further comprising an installation housing arranged between the centrifuge and the settling tank, and provided with passages, said settling tank being removably arranged on the installation housing, and said mixture inlet being arranged within the installation housing.

3. A separator as defined in claim 2, wherein said separator housing tapers towards the installation housing thereby defining a space around the taper of the separator housing, said mixture inlet being provided in said space.

4. A separator as defined in claim 3, wherein said connecting line passes through the space around the taper of the separator housing.

5. A separator as defined in claim 2, wherein said mixture inlet is formed on angle piece that can pivot about an axis that is perpendicular to the installation housing.

6. A separator as defined in claim 1, wherein the pump means is arranged coaxially with the centrifuge.

7. A separator as defined in claim 1, wherein the suction pipe of said pump means is provided with shielding baffles below the mixture inlet.

8. A separator as defined in claim 1, wherein said dental waste mixture is produced in a dental suction system having a suction air vacuum pump and an air separator, the mixture inlet being fitted with a non-return valve arranged on the pressure side of an auxiliary pump that removes the dental waste mixture from said air separator against the force of the suction air vacuum pump.

9. A separator as defined in claim 1, wherein said dental waste mixture is produced in a dental suction system having a suction air vacuum pump and an air separator, and wherein the outlet for discharging separated liquids is followed by an auxiliary pump that removes liquids from the separator against the force of the suction air vacuum pump, a non-return valve being arranged on the pressure side of the auxiliary pump.

10. A separator as defined in claim 1 connected to a dental suction system discharging said dental waste mixture out of a patient's mouth.

11. A separator as defined in claim 1 connected to a rinsing basin.

* * * * *

UNITED STATES PATENT AND TRADEMARK OFFICE
CERTIFICATE OF CORRECTION

PATENT NO. : 5,484,282
DATED : January 16, 1996
INVENTOR(S) : Trawoger et al.

It is certified that error appears in the above-indentified patent and that said Letters Patent is hereby corrected as shown below:

Column 4, Line 10: Delete "(2)" and insert -- 2(a) -- therefor;

Column 4, Line 30: Delete "cross-plate" and insert -- cross-piece -- therefor;

Column 4, Line 45: Delete "lines"; and

Column 6, Line 5: Insert -- an -- before "angle piece".

Signed and Sealed this

Sixth Day of August, 1996

Attest:

BRUCE LEHMAN

Attesting Officer        Commissioner of Patents and Trademarks